United States Patent
Kawate

(10) Patent No.: US 7,601,539 B2
(45) Date of Patent: Oct. 13, 2009

(54) STANDARD MATERIAL FOR PARTICLE ANALYZER

(75) Inventor: Yasunori Kawate, Kakogawa (JP)

(73) Assignee: Sysmex Corporation, Kobe-shi (JP)

( * ) Notice: Subject to any disclaimer, the term of this patent is extended or adjusted under 35 U.S.C. 154(b) by 393 days.

(21) Appl. No.: 11/483,560

(22) Filed: Jul. 11, 2006

(65) Prior Publication Data

US 2007/0013906 A1      Jan. 18, 2007

(30) Foreign Application Priority Data

Jul. 12, 2005   (JP)   .............................. 2005-203279

(51) Int. Cl.
*G01N 31/00*   (2006.01)
(52) U.S. Cl. .............................. 436/8; 436/10; 436/11; 436/16; 436/164; 436/166; 436/172; 356/300; 356/317; 356/318; 356/337
(58) Field of Classification Search ...................... 436/8, 436/10, 11, 16, 63, 164, 166, 172; 356/243.1–243.2, 356/300, 317–318, 337
See application file for complete search history.

(56) References Cited

U.S. PATENT DOCUMENTS 5,084,394 A      1/1992 Vogt et al.
5,888,823 A  *   3/1999 Matsumoto et al. ........... 436/10

2003/0219850 A1   11/2003 Tsuji et al.

FOREIGN PATENT DOCUMENTS

EP        0 774 655 A2    5/1997
WO        91/00509 A1     1/1991

OTHER PUBLICATIONS

Vogt et al.; "Model System Evaluating Fluorescein-Labeled Microbeads as Internal Standards to Calibrate Fluorescence Intensity on Flow Cytomer"; Cytometry; New York; US; vol. 10, No. 3; pp. 294-302; c. 1989.

* cited by examiner

*Primary Examiner*—Jill Warden
*Assistant Examiner*—Jameson Q Ma
(74) *Attorney, Agent, or Firm*—Sughrue Mion, PLLC

(57) ABSTRACT

A standard material that is used for judging an abnormal portion in a particle analyzer is described. The standard material comprises first standard particles to be fluorescence-stained by a fluorescence-staining treatment and second standard particles that have preliminarily contained a fluorescence dye.

A method and an analyzer that can judge an abnormal portion in a particle analyzer by using such a standard material are also described.

5 Claims, 7 Drawing Sheets

STANDARD MATERIAL FOR PARTICLE ANALYZER

BACKGROUND OF THE INVENTION

1. Field of the Invention

The present invention relates to a standard material for particle analyzer, which is used for quality control and the like on a particle analyzer.

2. Description of the Related Art

A particle analyzer, which stains particles in a biological sample such as urine and blood by using a fluorescent dye, and irradiates the particles with light so that the particles are classified and counted by measuring fluorescence and front scattered light emitted from the particles, has been known.

In such a particle analyzer, it is necessary to quality control the analyzer so as to always obtain accurate results of measurements. In other words, a standard material for quality control is measured by the particle analyzer, and if an accurate measured value is not obtained, the particle analyzer needs to be calibrated so that the measured value of the standard material is maintained in a predetermined range.

U.S. Pat. No. 5,888,823 has disclosed a standard fluid for use in a flow cytometer that is provided with a measurement sample preparing part that conducts a fluorescence-staining treatment on particle components in urine by using a dye and a fluorescence detector that detects fluorescence from the particle components that have been fluorescence-stained. This standard fluid contains standard particles. The standard particles are particles that can be stained through the fluorescence-staining treatment so as to show the same intensity of fluorescence as the particle components to be measured. In the case when any problem occurs in the measurement sample preparing part of the flow cytometer to cause a failure in properly conducting the staining process, an abnormality in the staining mechanism can be detected by measuring the standard particles.

In the case when a quality controlling operation is carried out on a particle analyzer by using the standard fluid disclosed in U.S. Pat. No. 5,888,823, even if the resulting measured value (intensity of fluorescence) is out of a predetermined range, for example, the sensitivity of the fluorescence detector is adjusted so that a calibrating process is carried out so as to obtain an appropriate measured value.

However U.S. Pat. No. 5,888,823 has disclosed nothing about a technique for measuring a standard material by using a particle analyzer and for judging any abnormal portion in the analyzer.

SUMMARY OF THE INVENTION

An objective of the present invention is to provide a standard material that is used for judging an abnormal portion in a particle analyzer. Moreover, another objective of the present invention is to provide a method and an analyzer that can judge an abnormal portion in a particle analyzer by using such a standard material.

A first aspect of the present invention relates to a standard material for a particle analyzer, the particle analyzer carrying out a fluorescence-staining treatment on measuring particles contained in a biological sample and analyzing the fluorescence-stained measuring particles, comprising: first standard particles which can be fluorescence-stained by the fluorescence-staining treatment; and second standard particles which have preliminarily contained a fluorescence dye.

A second aspect of the present invention relates to a method for judging an abnormal portion in a particle analyzer which comprises a measuring sample preparation unit for preparing a measuring sample by mixing a biological sample with a first fluorescence dye, a light source for irradiating the measuring sample with light and a fluorescence detector for detecting fluorescence from the measuring sample, comprising steps of: detecting first fluorescence from first standard particles and second fluorescence from second standard particles by using the particle analyzer; and judging the abnormal portion in the particle analyzer based upon the first fluorescence and the second fluorescence.

A third aspect of the present invention relates to a particle analyzer comprising: a measuring sample preparation unit for preparing a measuring sample by mixing a standard material containing first standard particles and second standard particles with a first fluorescence dye, the first standard particles being fluorescence-stained by the first fluorescence dye and the second standard particles preliminarily containing a second fluorescence dye; a light source for irradiating the measuring sample with light; a fluorescence detector for detecting first fluorescence from the first standard particles and second fluorescence from the second standard particles, contained in the measuring sample; and an analyzing unit for judging an abnormal portion in the particle analyzer based upon the first fluorescence and the second fluorescence.

A forth aspect of the present invention relates to a particle analyzer comprising: a measuring sample preparation unit for preparing a first measuring sample by mixing a first standard material containing first standard particles with a first fluorescence dye, and preparing a second measuring sample from a second standard material containing a second standard particles, the first standard particles being fluorescence-stained by the first fluorescence dye and the second standard particles preliminarily containing a second fluorescence dye; a light source for irradiating the first and second measuring samples; a fluorescence detector for detecting first fluorescence from the first standard particles contained in the first measuring sample and second fluorescence from the second standard particles contained in the second measuring sample; and an analyzing unit for judging an abnormal portion in the particle analyzer based upon the first fluorescence and the second fluorescence.

DESCRIPTION OF THE PREFERRED EMBODIMENTS

Figure 1:
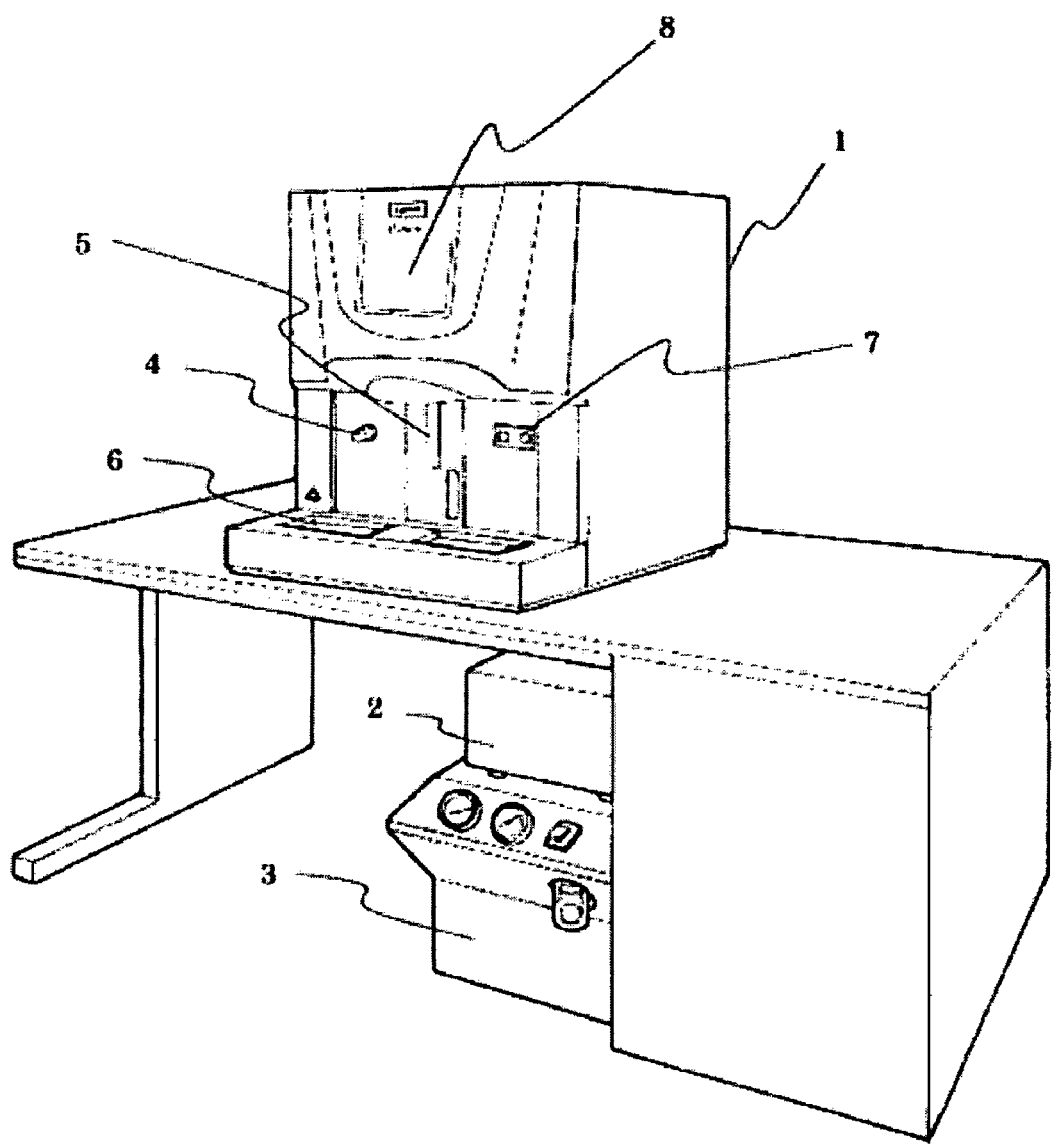
FIG. 1 is a drawing that shows the appearance of an analyzer for analyzing particle components in urea.

The standard material is used for a particle analyzer that carries out a fluorescence-staining treatment on measuring particles contained in a biological sample by using a dye and analyzes the measuring particles that have been fluorescence-stained. The standard material contains first standard particles that are fluorescence-stained by the fluorescence-staining treatment and second standard particles that are prepared so as to preliminarily contain a fluorescent dye. The first standard particles are fluorescence-stained in the fluorescence-staining treatment in the particle analyzer, and allowed to show an intensity of fluorescence. In contrast, the second standard particles, which preliminarily contain the fluorescent dye, show a predetermined intensity of fluorescence, although they are not stained actually. The measuring particles are particles which are contained in a biological sample such as urine and blood, and are to be measured in the particle analyzer. Examples of the measuring particles include, but are not limited to, white blood cells, red blood cells, epithelial cells, columnar cells and bacteria.

Upon measuring the standard material by the particle analyzer, the measured values of the first and second standard particles having different characteristics are respectively detected so that any abnormality in the analyzer can be detected with higher precision in comparison with conventional standard materials. More specifically, it becomes possible to presume a portion at which any abnormality is occurring in the particle analyzer. Consequently, upon calibrating the analyzer, a maintenance process and the like are appropriately carried out on the mechanism or the like that requires the calibration so that it is possible to preliminarily prevent any possible trouble that might occur in the future.

With respect to the first standard particles, particles, which are stained in the fluorescence-staining treatment so as to show the same degree of intensity of fluorescence as the measuring particles, are preferably used. Moreover, with respect to the second standard particles, particles, which have been preliminarily prepared so as to contain a fluorescent dye by using a proper method to show the same degree of intensity of fluorescence as the measuring particles, are preferably used.

The following description will discuss the standard material of the present embodiment. However, the present invention is not intended to be limited only by the present embodiment.

The standard material of the present embodiment is used for quality-controlling or calibrating a particle analyzer for analyzing particles contained in a biological sample. The standard material contains the first standard particles that are fluorescence-stained by the fluorescence-staining treatment and second standard particles that are prepared so as to preliminarily contain a fluorescent dye. The second standard particles, which contain the fluorescent dye, show a predetermined intensity of fluorescence.

With respect to the particle analyzer to which the standard particles of the present embodiment are applied, examples thereof include an analyzer which has a measurement sample preparing part for preparing a measuring sample by staining a biological sample such as urine and blood using a fluorescent dye. The analyzer prepares the measurement sample, supplies the prepared measuring sample to a flow cytometer, irradiates particles in the measuring sample passing through the flow cytometer with light, and detects fluorescence from the stained particles by a fluorescence detector. For example, the analyzer may include an analyzer for analyzing blood cell and an analyzer for analyzing particle components in urea (urinary sediment).

The following description will discuss an analyzer for analyzing particle components in urea, which is one example of a particle analyzer to which the standard particles of the present embodiment are applied. Here, this analyzer can measure white blood cells, red blood cells, epithelial cells, columnar cells and bacteria, as particles contained in urine. In particular, this analyzer has improved measuring precision for bacteria the size of which is smaller among the measuring particles. In this analyzer, with respect to bacteria, a diluting fluid used for measuring bacteria and a staining fluid used for measuring bacteria are applied, and with respect to the four particles other than the bacteria (white blood cells, red blood cells, epithelial cells and columnar cells), a diluting fluid and a staining fluid used for measuring the four particles are used so as to carry out the measurements. In the following description, the diluting fluid used for measuring the four particles is referred to as a first diluting fluid, the staining fluid used for measuring the four particles is referred to as a first staining fluid, the diluting fluid used for measuring bacteria is referred to as a second diluting fluid and the staining fluid used for measuring bacteria is referred to as a second staining fluid.

FIG. 1 shows the appearance of an analyzer for analyzing particle components in urea. This analyzer for analyzing particle components in urea is provided with a device main body 1, a laser power supply 2, and an air pressure supply 3. The device main body 1 is provided with a power-supply switch 4, a transporting unit 6 that transports a sample tube housing urine that is a biological sample and automatically supplies it to a suction unit 5, the suction unit 5 used for sucking the urine from the sample tube, a start switch 7 used for initiating the suction process for urine by the suction unit 5, and a touch-panel-type liquid crystal display 8 that receives inputs for operational instructions from the user, and displays information such as the results of analysis of the urine.

Figure 2:
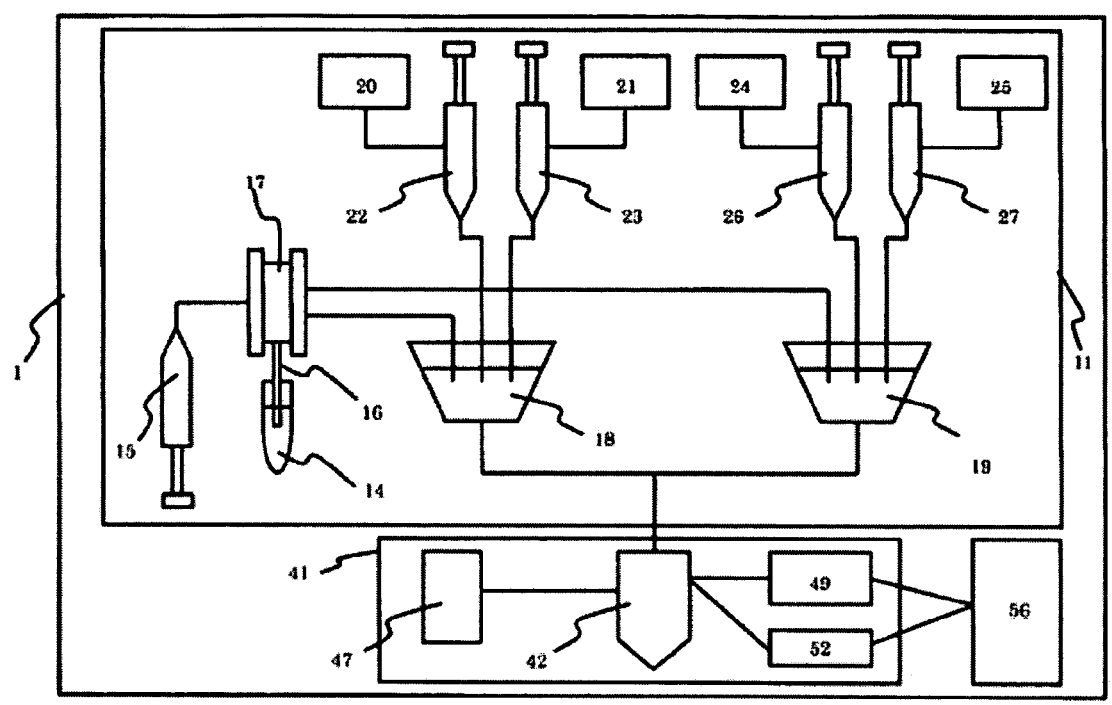
FIG. 2 is a schematic drawing that shows the inner structure of the analyzer for analyzing particle components in urea.

As shown in FIG. 2, the device main body 1 is provided with a sample preparing unit 11, a detection unit 41 and an analyzing unit 56. A biological sample (urine) in the test tube 14 is sucked through a suction pipette 16 by the operation of a syringe pump 15. The biological sample thus sucked is quantitatively measured by the sampling valve 17, and supplied and distributed respectively to reaction chambers 18 and 19. In other words, predetermined amounts of the biological sample are respectively delivered and supplied to the reaction chambers 18 and 19 from the same original biological sample. A container 20 housing the second diluting fluid (diluting fluid for bacteria) and a container 21 housing the second staining fluid (staining fluid for bacteria) are connected to the reaction chamber 18 so that predetermined amounts of the second diluting fluid and the second staining fluid are respectively supplied to the reaction chamber 18 by syringe pumps 22 and 23 through tubes; thus, a sample used for measuring bacteria (hereinafter, referred to as the measuring sample B) is prepared. Moreover, a container 24 housing the first diluting fluid (diluting fluid for the four particles) and a container 25 housing the first staining fluid (staining fluid for the four particles) are connected to the reaction chamber 19 so that predetermined amounts of the first diluting fluid and the first staining fluid are respectively supplied to the reaction chamber 19 by syringe pumps 26 and 27 through tubes; thus, a sample used for measuring the four particles (hereinafter, referred to as the measuring sample A) is prepared.

The detection unit 41 is used for detecting optical information such as fluorescence and scattered light from the respective particles contained in the measuring sample, and is comprised of a flow cytometer. The flow cytometer is provided with a flow cell 42 that allows the measuring sample to flow, a laser light source 47 that irradiates the measuring sample flowing through the flow cell 42 with laser light, a photo-multiplier tube 52 that receives side fluorescence emitted from the particles in the measuring sample and a photodiode 49 that receives front scattered light.

Figure 3:
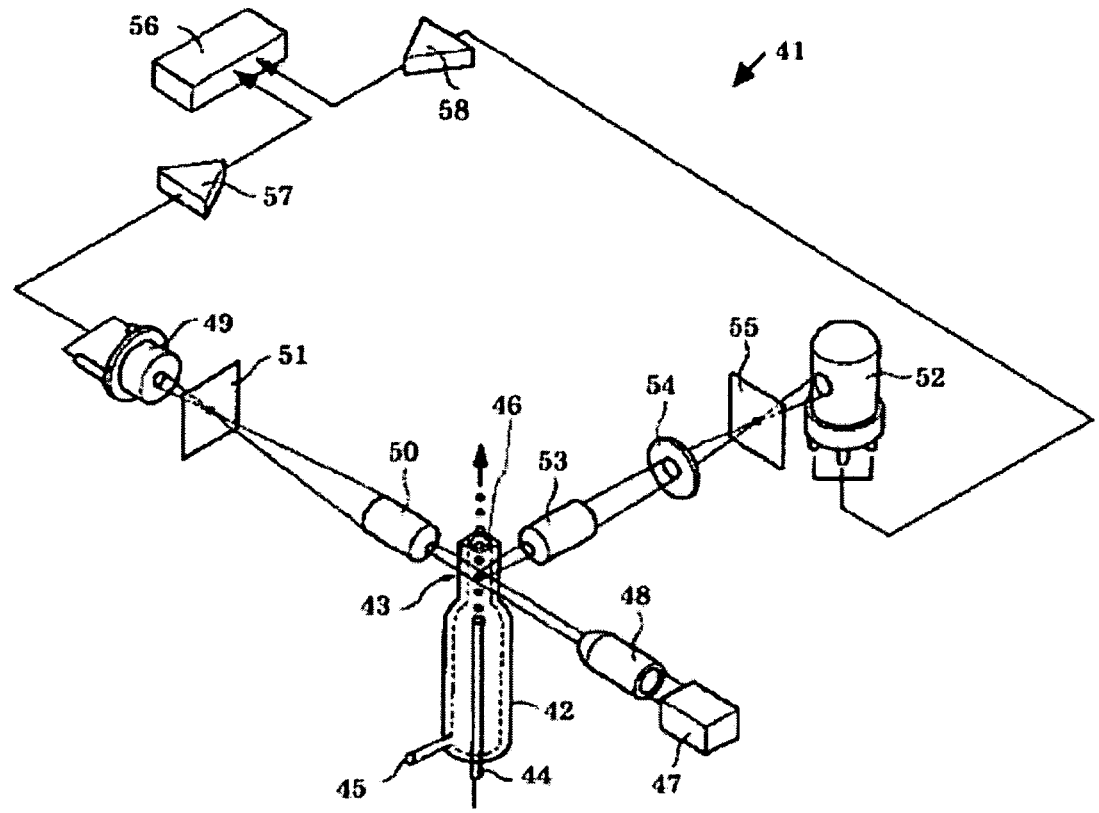
FIG. 3 is a drawing that explains a flow cytometer that serves as a detection unit of the analyzer for analyzing particle components in urea.

FIG. 3 shows the flow cytometer in detail. As shown in FIG. 2, the reaction chambers 18 and 19 are connected to the flow cell 42. The flow cell 42, which allows the measuring sample to flow, forms a portion to which the laser light is directed, and is provided with an orifice portion 43 in which an inner flow path is narrowed, a nozzle 44 that discharges the measuring sample upward toward the orifice portion, a sheath fluid supplying port 45 and a waste fluid port 46. The laser light source 47 is a red semiconductor laser light source that emits laser light having a wavelength of 633 nm. The detection unit 41 is provided with a condenser lens 48 that condenses the laser light applied from the laser light source 47 onto the flow cell 42, a photodiode 49 that receives the front scattered light emitted from particles in the measuring sample irradiated with the laser light, and converts the scattered light into an electric signal, a collector lens 50 and a pinhole 51 used for condensing the front scattered light onto the photodiode 49, a photo-multiplier tube 52 that receives fluorescence emitted from the particles of the measuring sample irradiated with the laser light, and converts it an electric signal, a collector lens 53, a filter 54 and a pinhole 55 that are used for condensing the fluorescence onto the photo-multiplier tube 52, and amplifiers 57 and 58 that amplify electric signals outputted from the photodiode 49 and the photo-multiplier tube 52, and output the resulting signals to an analyzing unit 56 as a front scattered light signal and a fluorescence signal. When the measuring sample is allowed to flow the flow cell 42, fluorescence and scattered light are generated, each time each of the particles contained in the measuring sample crosses the irradiation area of the laser light applied by the laser light source 47. The photo-multiplier tube 52 and the photodiode 49 respectively receive and photo-electric convert side fluorescence and front scattered light, and output the resulting signals to the analyzing unit 56 as photo-detection signals such as a side fluorescence signal and a front scattered light signal.

The analyzing unit 56 in FIG. 3 is constituted by circuits that amplify a photo-detection signal for each of the particles detected in the detection unit 41 and eliminate noises, and a computer constituted by a CPU, ROM, RAM and the like. The analyzing unit 56 stores a photo-detection signal detected by the detection unit 41 for each of the particles. Moreover, the analyzing unit 56 analyzes the photo-detection signal stored therein, and forms a two-dimensional distribution chart so that the particles contained in the measuring sample are counted. The signal intensity is obtained from the peak level of pulses in the photo-detection signal. The intensity of the fluorescence signal indicates the intensity of fluorescence detected from each of the particles in the measuring sample, and forms a parameter that indicates the degree of staining by the fluorescent dye. The intensity of the front scattered light corresponds to an intensity of the front scattered light detected from each of the particles in the measuring sample, and forms a parameter that indicates the size of each particle.

By combining these parameters, the two-dimensional distribution chart is formed. Particles appearing on the distribution chart are calculated as dots of particles that appear within areas that are set in accordance with the respective appearance positions of the particles contained in the measuring sample so that the results of the measurements are obtained.

Here, as shown in FIG. 2, the analyzing unit 56 is connected to the touch-panel-type liquid crystal display 8. The results of measurements obtained by the analysis in the analyzing unit 56 are displayed on the touch-panel-type liquid crystal display 8.

The following description will discuss the standard material for an analyzer for analyzing particle components in urea by means of examples. The standard material is comprised of standard particles that correspond to measuring particles and a solvent used for dispersing the standard particles. The standard particles include first standard particles that can be stained by a dye virtually in the same manner as the measuring particles and second standard particles that are preliminarily prepared so as to contain a fluorescent dye. Here, the first standard particles stained by the dye are allowed to show an intensity of fluorescence that is within the distribution range of the intensity of fluorescence detected from the measuring particles that have been stained by the dye. Moreover, the second standard particles, which actually are not stained by the dye, are also allowed to show an intensity of fluorescence that is within the distribution range of the intensity of fluorescence detected from the measuring particles that have been stained by the dye.

In the following description, one example of a standard material in which standard particles for white blood cells, which deal with white blood cells, are used as the first standard particles, while standard particles for bacteria, which deal with bacteria, are used as the second standard particles, is prepared, and this standard material is measured by the above-mentioned analyzer 1 for analyzing particle components in urea.

(Standard Particles)

With respect to the standard particles for bacteria, fluorescent latex particles having an average particle size of 1 μm (DUKE4010A+fluorescence 1.0%, made by Duke Co., Ltd.) were used. Here, vinyl acetate polymer particles having an average particle size of 7 μm were used as the standard particles for white blood cells.

(Preparation of Buffer Solution 1 and Buffer Solution 2)

To 1 L of refined water were added 0.3% of sodium chloride, 0.08% of an antiseptic agent and 0.035% of acetic acid so that a buffer solution 1 was prepared. Moreover, sodium chloride was added to this buffer solution 1 so that the final concentration was set to 1.65%, and to this was further added glycerin so that the final concentration was set to 9.0%; thus, a buffer solution 2 was prepared.

(Preparation of Suspension of Standard Particles for Bacteria)

To 250 μl of fluorescent latex particles (500 particles/μl) was added 1 ml of 6% polyvinyl alcohol solution, and this was stirred by using a vortex so that fluorescent latex particles were suspended. A sonicator having a horn diameter of 8 mm was set to 50 mW for 30 seconds, and the fluorescent latex particles in the suspension were coated with polyvinyl alcohol. To this suspension was added an appropriate amount of the buffer solution 1 to be washed, and this was centrifuged at 12000 rpm so that a supernatant fluid was removed. After this washing process had been repeated twice, 2 ml of the buffer solution 2 was added to this so that a suspension of standard particles for bacteria was prepared.

(Preparation of Suspension of Standard Particles for White Blood Cells)

To 250 μl of vinyl acetate polymer particles (200 particles/μl) was added an appropriate amount of the buffer solution 1 to be washed, and this was centrifuged at 3000 rpm so that a supernatant fluid was removed. After this washing process had been repeated twice, 2 ml of the buffer solution 2 was added to this so that a suspension of standard particles for white blood cells was prepared.

The suspension of standard particles for bacteria and the suspension of standard particles for white blood cells, prepared by the above-mentioned processes, were mixed and used as a standard material.

(Preparation of Diluting Fluid for Measuring the Four Particles (First Diluting Fluid))

HEPES (50 mM), EDTA-3K (0.40%), 2-phenoxy ethanol (0.75%), sodium propionate (0.6%), sodium hydroxide (0.052%), Tomicide S (350 ppm), Proxel GX-L (350 ppm) and refined water (1 L) were mixed to prepare a first diluting fluid.

(Preparation of Diluting Fluid for Measuring Bacteria (Second Diluting Fluid))

Citric acid (100 mM), sodium sulfate (90 mM), amide sulfuric acid (100 mM), tetradecyltrimethylammonium bromide (0.1%) and sodium hydroxide the amount of which had been adjusted to pH 2.5 were mixed to prepare a second diluting fluid.

(Preparation of Staining Fluid for Measuring the Four Particles (First Staining Fluid))

NK-529 (made by Nippon Kankoh-Shikiso Kenkyusho Co., Ltd.) serving as a fluorescent dye represented by the following chemical formula 1 (240 ppm) and NK-136 (made by Nippon Kankoh-Shikiso Kenkyusho Co., Ltd.) serving as a fluorescent dye represented by the following chemical formula 2 (25.2 ppm) were dissolved in ethylene glycol so that a first staining fluid was prepared.

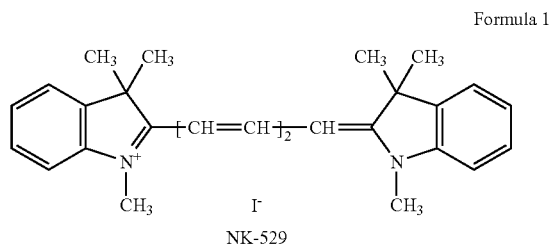

Formula 1

NK-529

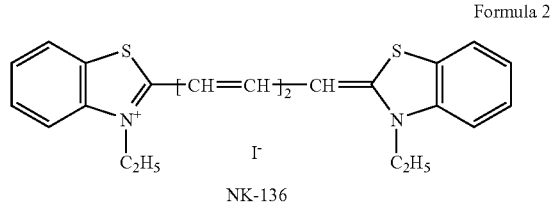

Formula 2

NK-136

(Preparation of Staining Fluid for Measuring Bacteria (Second Staining Fluid))

A fluorescent dye represented by the following chemical formula 3 was dissolved in ethylene glycol to be set to 40 ppm that a second staining solution was prepared.

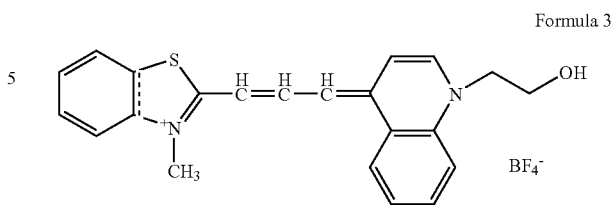

Formula 3

Figure 4:
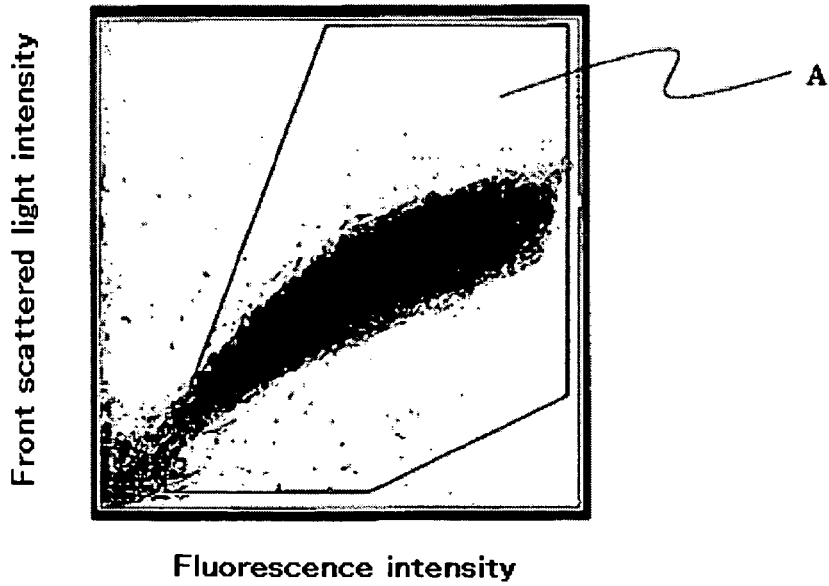
FIG. 4 is a drawing that indicates the results of measurements on bacteria by the analyzer for analyzing particle components in urea.
Figure 5:
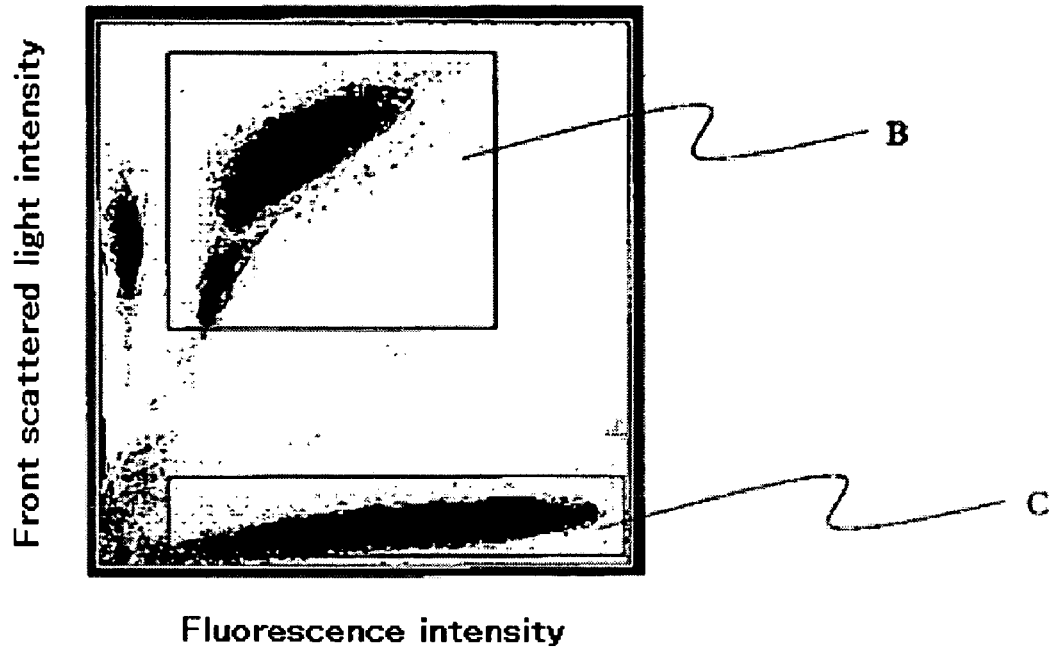
FIG. 5 is a drawing that indicates the results of measurements on while blood cells by the analyzer for analyzing particle component in urea.

In the analyzer 1 for analyzing particle components in urea, first, the second diluting fluid was set in a container 20, the second staining fluid was set in a container 21, the first diluting fluid was set in a container 24 and the first staining fluid was set in a container 25, respectively, and a urine sample was measured. FIGS. 4 and 5 show distribution charts in which the intensity of front scattered light, detected by the photodiode 49, was plotted on the axis of ordinates and the intensity of side fluorescence, detected by the photo-multiplier tube 52, was plotted on the axis of abscissas. Here, FIG. 4 is a distribution chart in which the front scattered light intensity is raised in comparison with that of FIG. 5.

FIG. 4 shows the results of measurements obtained from the urine sample and the measuring sample B prepared by the second diluting fluid and the second staining fluid. In the distribution chart of FIG. 4, the front scattered light sensitivity is raised so as to measure bacteria contained in the urine sample, and bacteria were observed in an A area (front scattered light intensity: about 70 to 110 channels, fluorescence intensity: about 100 to 160 channels) in the Figure.

FIG. 5 shows the results of measurements obtained from the urine sample and the measuring sample A prepared by the first diluting fluid and the first staining fluid. In the distribution chart of FIG. 5, the front scattered light sensitivity is set to a lower level in comparison with that of FIG. 4 so that bacteria were observed in a C area, while white blood cells were observed in a B area (front scattered light intensity: about 170 to 230 channels, fluorescence intensity: about 30 to 170 channels) in the Figure.

Figure 6:
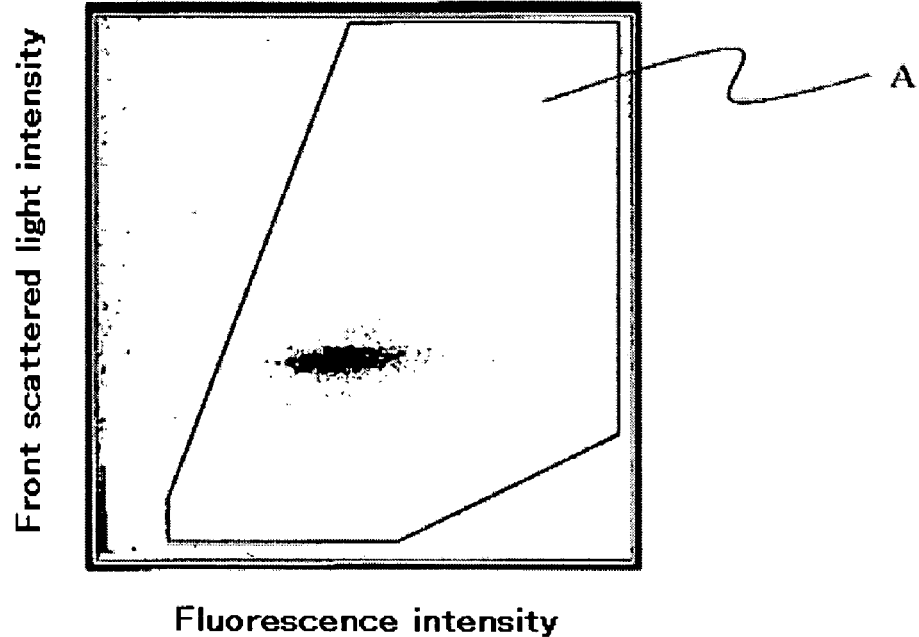
FIG. 6 is a drawing that indicates the results of measurements on standard particles for bacteria relating to an embodiment of the present invention by the analyzer for analyzing particle component in urea.
Figure 7:
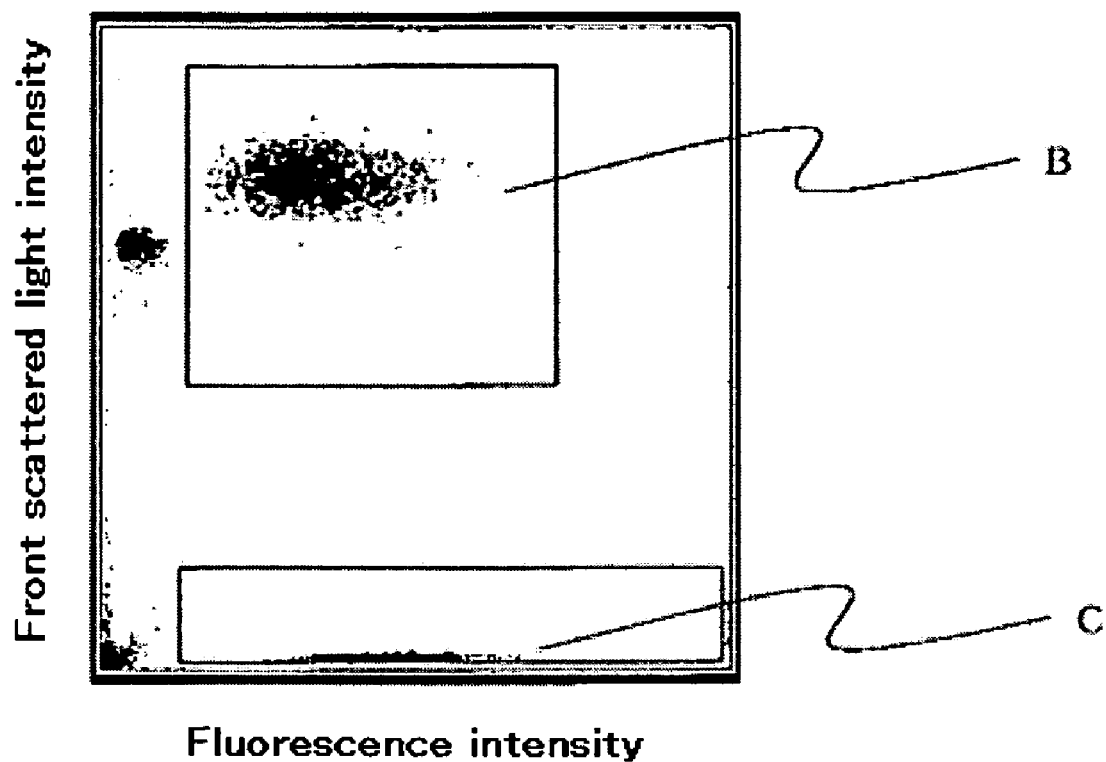
FIG. 7 is a drawing that indicates the results of measurements on standard particles for white blood cells relating to the embodiment of the present invention by the analyzer for analyzing particle component in urea.

Next, measurements were carried out on the standard material by using the analyzer 1 for analyzing particle components in urea. FIGS. 6 and 7 show the resulting distribution charts. FIG. 6 shows the results of measurements obtained from the standard material and the measuring sample B prepared by the second diluting fluid and the second staining fluid. FIG. 7 shows the results of measurements obtained from the standard material and the measuring sample A prepared by the first diluting fluid and the first staining fluid. FIGS. 6 and 7 show distribution charts in which the intensity of front scattered light was plotted on the axis of ordinates and the intensity of side fluorescence was plotted on the axis of abscissas. In the same manner as FIGS. 4 and 5, FIG. 6 is a distribution chart in which the front scattered light intensity is raised in comparison with that of FIG. 7.

In FIG. 6, the standard particles for bacteria (fluorescent latex particles) were observed in the A area that was an appearance area of bacteria. The distribution range of the standard particles for bacteria was positioned virtually in the middle of the appearance area A of bacteria, and observed with the front scattered light intensity being set in about 81 to 88 channels and the fluorescence intensity being set in about 110 to 140 channels. Here, the standard particles for bacteria were particles that actually were not stained by the second staining fluid.

In FIG. 7, the standard particles for white blood cells (vinyl acetate polymer particles) were observed in the B area that was an appearance area of white blood cells. The distribution range of the standard particles for white blood cells was observed, with the front scattered light intensity being set in about 200 to 220 channels and the fluorescence intensity being set in about 30 to 140 channels. Moreover, the standard particles for bacteria were observed at an area C. Here, the standard particles for bacteria were particles that actually were not stained by the first staining fluid.

In FIG. 7, the appearance area of the standard particles for white blood cells (vinyl acetate polymer particles) and the appearance area of the standard particles for bacteria (fluorescent latex particles) are indicated; in contrast, in FIG. 6, the appearance area of the standard particles for white blood cells is not clearly-indicated. This is because FIG. 6 is a distribution chart in which the front scattered light sensitivity is raised so as to measure the bacteria in the sample. As described earlier, there is a big difference in the particle size between the standard particles for bacteria and the standard particles for white blood cells. Since the front scattered light forms a parameter that reflects the size of the particles, the intensity of front scattered light obtained from the standard particles for bacteria and the intensity of front scattered light obtained from the standard particles for white blood cells are different from each other in their sizes. Therefore, with respect to FIG. 6, by forming a distribution chart with a reduced sensitivity of the front scattered light, the appearance area of the standard particles for white blood cells can be confirmed.

Upon analyzing a urine sample by using the analyzer for analyzing particle components in urea 1, the intensity of fluorescence of particles to be detected is determined by the following factors:

(1) Conditions of the detection unit 41: for example, the sensitivity (output voltage) of a fluorescence detector (photomultiplier tube 52), and (2) Conditions of the sample preparation unit 11: for example, the amount of supply of the staining fluid.

Here, it is supposed that the average of the fluorescence intensity obtained by measurements of standard particles is compared with a predetermined range of fluorescence intensity, and that the results are judged and classified into ± (values within a normal range), + (values higher than the normal range by 10 channels) and − (values lower than the normal range by 10 channels). For example, in the case when the results of judgment of the first standard particles and the second standard particles obtained from the measuring sample A are indicated by values in the following Table 1, it can be judged that there is any abnormality in the detection unit 41 and the sample preparation unit 11 (particularly in a portion relating to preparation of the measuring sample A).

TABLE 1

| | Results of Judgment | Portion with abnormality (Example of Possible Cause) |
|---|---|---|
| First Standard Particles | + | Sample Preparation Unit |
| Second Standard Particles | ± | (Much amount of staining fluid, etc.) |
| First Standard Particles | + | Detection Unit |
| Second Standard Particles | + | (High sensitivity of fluorescence detector, etc.) |
| First Standard Particles | ± | Sample Preparation Unit |
| Second Standard Particles | − | and Detection Unit (Much amount of staining fluid, low sensitivity of fluorescence detector, etc.) |
| First Standard Particles | − | Sample Preparation Unit |
| Second Standard Particles | ± | (Less amount of staining fluid, etc.) |

TABLE 1-continued

| | Results of Judgment | Portion with abnormality (Example of Possible Cause) |
|---|---|---|
| First Standard Particles | − | Detection Unit |
| Second Standard Particles | − | (Low sensitivity of fluorescence detector, etc.) |
| First Standard Particles | − | Sample Preparation Unit |
| Second Standard Particles | + | and Detection Unit (Less amount of staining fluid, high sensitivity of fluorescence detector, etc.) |

Figure 8:
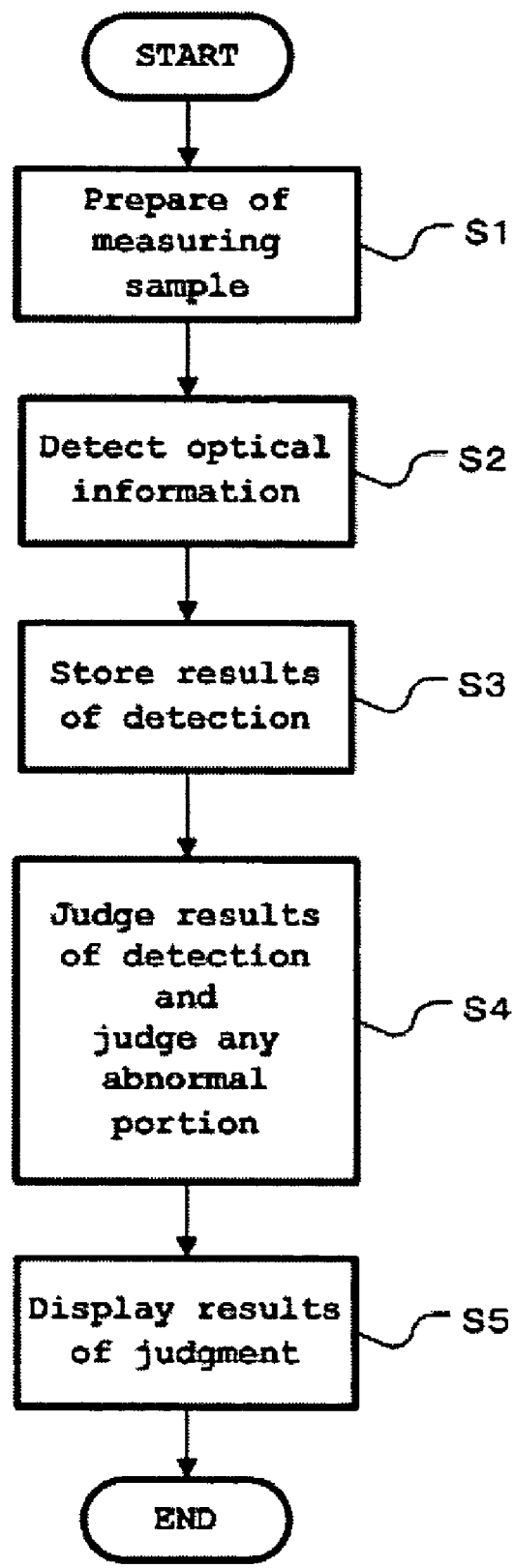
FIG. 8 is a flow chart that shows judging processes of any abnormal portion in the analyzer for analyzing particle component in urea.

Moreover, in the same manner, with respect to the results of judgment on the first standard particles and the second standard particles obtained from the measuring sample B, by carrying out the above-mentioned examinations, it can be judged if there is any abnormality in the detection unit 41 and the sample preparation unit 11 (particularly in a portion relating to preparation of the measuring sample B). Here, the analyzer for analyzing particle components in urea 1 relating to the present embodiment is designed to automatically conduct the above-mentioned judgment on any abnormal portion. Referring to FIG. 8, the following description will discuss operations in this case.

First, the user sets a standard material containing the first standard particles and the second standard particles at a predetermined position, and when a start switch 7 is pressed, the suction process for the standard material is initiated.

Step 1 (S1): At S1, the measuring sample A and the measuring sample B are prepared.

First, the standard material in a test tube 14 is sucked through a suction pipette 16 by the operation of a syringe pump 15. The standard material thus sucked is quantitatively measured by a sampling valve 17, and separately supplied to reaction chambers 18 and 19. A predetermined amount of the second diluting fluid in a container 20 is supplied to the reaction chamber 18 through a tube by a syringe pump 22. A predetermined amount of the second staining fluid in the container 21 is supplied to the reaction chamber 18 through a tube by a syringe pump 23. Thus, the measuring sample B is prepared. A predetermined amount of the first diluting fluid in a container 24 is supplied to the reaction chamber 19 through a tube by a syringe pump 26. A predetermined amount of the first staining fluid in the container 25 is supplied to the reaction chamber 19 through a tube by a syringe pump 27. Thus, the measuring sample A is prepared.

Step 2 (S2): At S2, the fluorescence intensity and front scattered light intensity are obtained based upon the first standard particles and the second standard particles contained in the respective measuring samples.

First, the measuring sample A in the reaction chamber 19 is discharged into a flow cell through the nozzle 44. Simultaneously, a sheath fluid is discharged into a sheath flow cell from the sheath fluid supplying port 45. Thus, the measuring sample A is surrounded by the sheath fluid in the flow cell, and further narrowed thinly by the orifice portion 43, and allowed to flow. A laser light beam emitted from the laser light source 47 is condensed by the condenser lens 48, and directed onto the measuring sample A flowing through the orifice portion 43. Front scattered light, released from the first standard particles and the second standard particles in the measuring sample A upon receipt of the laser light beam, is received by the photodiode 49, and photo-electric converted to be outputted as a front scattered light signal. Side fluorescence, emitted from the first standard particles and the second standard particles in the measuring sample A, is received by the photomultiplier 52, and photo-electric converted to be outputted as a side fluorescence signal. The respective signals are outputted to the analyzing unit 56. The analyzing unit 56 analyzes the front scattered light signal and the side fluorescence signal detected by the detection unit 41 so that a front scattered light intensity and a fluorescence intensity are obtained. Thus, the first fluorescence intensity and the first front scattered light intensity are obtained from the first standard particles in the measuring sample A. Moreover, the second fluorescence intensity and the second front scattered light intensity are obtained from the second standard particles in the measuring sample A.

In the same manner, the measuring sample B in the reaction chamber 18 is discharged into a flow cell through the nozzle 44, and allowed to flow through the flow cell. Front scattered light, released from the first standard particles and the second standard particles in the measuring sample B upon receipt of the laser light beam, is received by the photodiode 49, and photo-electric converted to be outputted as a front scattered light signal. Side fluorescence, emitted from the first standard particles and the second standard particles in the measuring sample B, is received by the photo-multiplier tube 52, and photo-electric converted to be outputted as a side fluorescence signal. The respective signals are outputted to the analyzing unit 56. The analyzing unit 56 analyzes the front scatter light signal and the side fluorescence signal detected by the detection unit 41 so that a front scattered light intensity and a fluorescence intensity are obtained. In this manner, the third fluorescence intensity and the third front scattered light intensity are obtained from the first standard particles in the measuring sample B. Moreover, the fourth fluorescence intensity and the fourth front scattered light intensity are obtained from the second standard particles in the measuring sample B.

Step 3 (S3): At S3, the analyzing unit 56 stores the front scattered light intensity and the fluorescence intensity obtained at S2.

Step 4 (S4): At S4, the analyzing unit 56 obtains the results of judgment on the fluorescence intensity of the first standard particles and the results of judgment on the fluorescence intensity of the second standard particles, and based upon the results of judgment, judges any abnormal portion based upon the same criteria as shown in Table 1.

First, with respect to the first fluorescence intensity thus obtained, the analyzing unit 56 calculates an average value thereof (hereinafter, referred to as average value X). Here, when the resulting average value X is within a range between predetermined upper limit and lower limit values, the analyzing unit 56 judges this state as ± (value inside of a normal range); when it exceeds the upper limit value, the analyzing unit 56 judges this state as + (value higher than the normal range); and when it goes below the lower limit value, the analyzing unit 56 judges this state as − (value lower than the normal range). In the same manner, with respect to the second fluorescence intensity, the third fluorescence intensity and the fourth fluorescence intensity, the analyzing unit 56 respectively calculates the average values and carries out the same judging processes.

In this manner, the results of judgment relating to the fluorescence intensity of the first standard particles (the first fluorescence intensity and the third fluorescence intensity) and the results of judgment relating to the fluorescence intensity of the second standard particles (the second fluorescence intensity and the fourth fluorescence intensity) are obtained, and based upon the results of judgment, any abnormal portion is judges based upon the same criteria as shown in Table 1.

Step 5 (S5): At S5, the results of judgment for any abnormal portion at S4 are outputted to the touch-panel type liquid crystal display 8.

As described above, the use of the standard particles in accordance with the present embodiment makes it possible to detect an abnormality as in the case of a reduction of the fluorescence staining property in the sample preparing part with a raised sensitivity in the fluorescence detector, which has not been detected by the prior art. Moreover, since a portion having the abnormality can be detected, it becomes possible to easily carry out the corresponding maintenance process for the device appropriately.

In the above-mentioned embodiment, the explanation has been given by exemplifying a case in which any abnormal portion is detected by measuring the intensity of fluorescence of the standard particles; however, the detection of any abnormal portion can also be carried out by measuring the pulse width of fluorescence. Moreover, the presence of any abnormality in the scattered light detector can be confirmed by measuring not only the fluorescence of the standard particles, but also the scattered light (intensity or pulse width) thereof.

Figure 9:
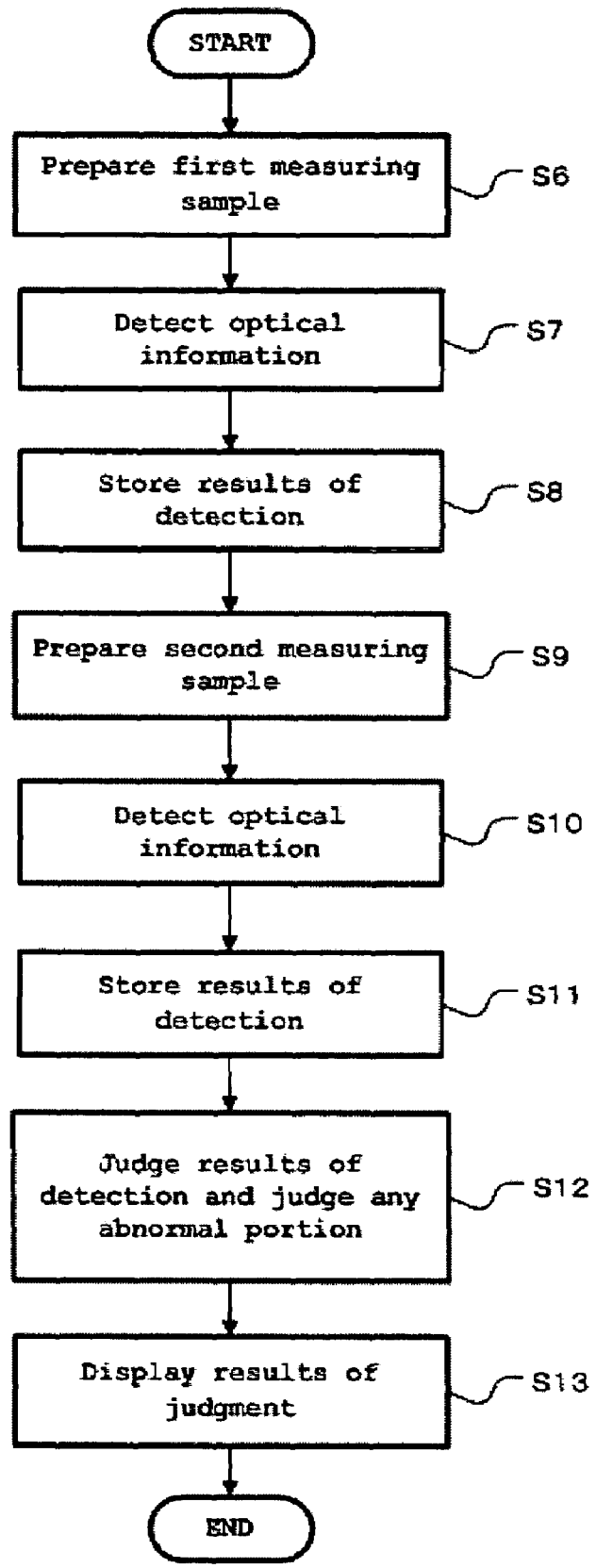
FIG. 9 is another flow chart that shows judging processes of any abnormal portion in the analyzer for analyzing particle component in urea.

In the above-mentioned embodiment, a measuring process in which the standard material containing the first standard particles and the second standard particles is used has been explained; however, the present invention is not intended to be limited by this process. For example, the first standard material containing the first standard particles and the second standard material containing the second standard particles may be used. Referring to FIG. 9, the following description will discuss operations in this case.

First, the user sets a first standard material containing the first standard particles and a second standard material containing the second standard particles at predetermined positions, and when a start switch 7 is pressed, suction processes for the first standard material and the second standard material are successively initiated.

Step 6 (S6): At S6, the first measuring sample A and the first measuring sample B are prepared from the first standard material. With respect to the operations of the devices relating to the preparation for the respective measuring samples, the same operations as those of the above-mentioned S1 are carried out.

Step 7 (S7): At S7, the fluorescence intensity and the front scattered light intensity are obtained from the first standard particles and the second standard particles contained in the respective measuring samples obtained at the above-mentioned S6. With respect to the operations of the devices used for acquiring the fluorescence intensity and the front scattered light intensity, the same operations as those of the above-mentioned S2 are carried out. Thus, the first fluorescence intensity and the first front scattered light intensity are obtained from the first standard particles in the first measuring sample A prepared in the above-mentioned S6. Moreover, the third fluorescence intensity and the third front scattered light intensity are obtained from the first standard particles in the measuring sample B.

Step 8 (S8): At S8, the analyzing unit 56 stores the front scattered light intensity and the fluorescence intensity obtained at S7.

Step 9 (S9): At S9, the second measuring sample A and the second measuring sample B are prepared from the second standard material. With respect to the operations of the devices relating to the preparation for the respective measuring samples, the same operations as those of the above-mentioned S1 are carried out.

Step 10 (S10): At S10, the fluorescence intensity and the front scattered light intensity are obtained from the first standard particles and the second standard particles contained in the respective measuring samples obtained at the above-mentioned S9. With respect to the operations of the devices used for acquiring the fluorescence intensity and the front scattered light intensity, the same operations as those of the above-mentioned S2 are carried out. Thus, the second fluorescence intensity and the second front scattered light intensity are obtained from the first standard particles in the second measuring sample A prepared in the above-mentioned S9. Moreover, the fourth fluorescence intensity and the fourth front scattered light intensity are obtained from the first standard particles in the measuring sample B.

Step 11 (S11): At S11, the analyzing unit 56 stores the front scattered light intensity and the fluorescence intensity obtained at the above-mentioned S10.

Step 12 (S12): At S12, the analyzing unit 56 obtains the results of judgment on the fluorescence intensity of the first standard particles and the results of judgment on the fluorescence intensity of the second standard particles, and based upon the results of judgment, judges any abnormal portion based upon the same criteria as shown in Table 1. With respect to the operations of the devices relating to the judgment on the results of detection and the judgment on any abnormal portion, the same operations as those of the above-mentioned S4 are carried out. In this manner, the results of judgment on the fluorescence intensity of the first standard particles (the first fluorescence intensity and the third fluorescence intensity) and the results of judgment on the fluorescence intensity of the second standard particles (the second fluorescence intensity and the fourth fluorescence intensity) are obtained, and based upon the results of judgment, any abnormal portion is judged based upon the same criteria as shown in Table 1.

Step 13 (S13): At S13, the results of judgment on any abnormal portion at S12 are outputted to the touch-panel type liquid crystal display 8.

Here, at S5 or S13, not only the results of judgment on any abnormal portion, but also the status of the first standard particles and the second standard particles, that is, ±, + or −, can be displayed on the touch-panel type liquid crystal display 8.

In the above-mentioned embodiment, standard particles for white blood cells are used as the standard particles corresponding to the first standard particles, while standard particles for bacteria are used as the standard particles corresponding to the second standard particles; however, the present invention is not limited by this arrangement. For example, in addition to the standard particles for white blood cells, standard particles for red blood cells, standard particles for epithelial cells, standard particles for columnar cells and the like may be used, as the first standard particles.

With respect to the standard particles for white blood cells that deal with white blood cells, for example, vinyl acetate polymer particles and porous silica particles can be used. These standard particles are particles that are allowed to show virtually the same intensity of fluorescence as that of white blood cells, when stained by using a dye. Moreover, these standard particles are preferably prepared as particles that show virtually the same intensity of scattered light as that of white blood cells, and the average particle size is preferably set in a range from 5 to 15 µm, more preferably, from 7 to 12 µm.

With respect to the standard particles for epithelial cells that deal with epithelial cells, materials such as polyacrylamide particles, cellulose gel and hydrophilic vinyl polymer gel may be used. These standard particles are particles that are allowed to show virtually the same intensity of fluorescence as that of epithelial cells, when stained by using a dye. Moreover, these standard particles are preferably prepared as particles that show virtually the same intensity of scattered light as that of epithelial cells, and the average particle size is preferably set in a range from 20 to 150 µm, more preferably, from 45 to 90 µm.

With respect to the standard particles for columnar cells that deal with columnar cells, materials such as hydrophilic vinyl polymer particles and crosslinked agarose gel may be used. These standard particles are particles that are allowed to show virtually the same intensity of fluorescence as that of columnar cells, when stained by using a dye. Moreover, these standard particles are preferably prepared as particles that show virtually the same intensity of scattered light as that of columnar cells, and the average particle size is preferably set in a range from 5 to 60 µm, more preferably, from 10 to 40 µm.

With respect to the standard particles for red blood cells that deal with red blood cells, for example, latex particles and high-purity silica particles can be used. These standard particles are particles that are allowed to show virtually the same intensity of fluorescence as that of red blood cells, when stained by using a dye. Moreover, these standard particles are preferably prepared as particles that show virtually the same intensity of scattered light as that of red blood cells, and the average particle size is preferably set in a range from 3 to 20 µm, more preferably, from 5 to 10 µm.

With respect to the standard particles for bacteria that deal with bacteria, for example, fluorescent latex particles can be used. These standard particles are preferably prepared as particles that actually are not stained by a dye used in the particle analyzer. Moreover, those particles that show virtually the same intensity of fluorescence as that of bacteria fluorescence-stained by the dye are preferably used. Furthermore, those particles that show virtually the same intensity of scattered light as that of bacteria are preferably used, and the average particle size is preferably set in a range from 0.5 to 5 µm, more preferably, from 0.8 to 3 µm.

In the present embodiment, fluorescent latex particles are used as the standard particles corresponding to bacteria, and those particles that are fluorescence-stained by the fluorescence staining treatment in the particle analyzer are used as the standard particles corresponding to white blood cells; however, the present invention is not intended to be limited by this arrangement. For example, those particles that are fluorescence-stained virtually in the same manner as bacteria by a dye may be used as the standard particles corresponding to bacteria, and fluorescent particles, preliminarily prepared so as to contain a fluorescent dye, may be used as the standard particles corresponding the white blood cells, red blood cells, epithelial cells or columnar cells. Here, in order to improve the dispersing property of the latex particles and the like used as the standard particles, the latex particles may be coated with polyvinyl alcohol.

With respect to a solvent used for the standard material, an aqueous solvent may be used, and a buffer solution is preferably used. In order to improve the dispersing property of the standard particles, a dispersibility-improving agent such as a surfactant may be added to the buffer solution.

With respect to reagents that are mixed with a urine sample to prepare a measuring sample, as described in the above-mentioned embodiment, the first staining fluid and the first diluting fluid used for measuring red blood cells, white blood cells, epithelial cells and columnar cells, as well as the second staining fluid and the second diluting fluid used for measuring bacteria, are preferably used respectively. This is because, since bacteria are minute in comparison with the other particles, the diluting fluid and staining fluid exclusively used for measuring bacteria are applied so that the measuring precision for bacteria can be improved.

For example, the urine sample often includes so-called impurities, that is, mucous fibers, crystals, non-crystalline salts, fragments of cells and the like, and because of similar sizes, they intervene with the measurements on bacteria. The intensity of front scattered light detected from the impurities is overlapped with the intensity detected from bacteria, making it difficult to distinguish these. For this reason, it is preferable to prepare such a second diluting fluid that can suppress the impurities from being stained, and can also dissolve the impurities.

In order to improve the staining property of bacteria, suppress the impurities from being stained and dissolve the impurities to a certain degree, the second diluting fluid is preferably prepared with a pH range from 2.0 to 4.5, preferably, from 2.0 to 3.0.

In order to property maintain the pH of the second diluting fluid, acid or a buffer agent of pKa 1 to 5 can be used. Although not particularly limited as long as the above-mentioned pH range can be maintained, preferable examples thereof include: citric acid salt, phosphoric acid salt, phthalic acid salt, glycine, succinic acid, lactic acid, β-alanine, ε-aminocaproic acid and fumaric acid. The amount of use is preferably set so as to maintain the above-mentioned pH range, and ranges from 10 to 500 mM.

By adding a surfactant, more preferably, a cationic surfactant, to the second diluting fluid, the cell membrane of bacteria is damaged to allow the dye to more easily intrude therein. As a result, the bacteria are more effectively stained to be more easily distinguished from the impurities. Moreover, mucous fibers, red blood cells, fragments of cells and the like are dissolved or allowed to contract so that adverse effects to the bacteria detection can be reduced.

With respect to the cationic surfactant, although not particularly limited, the quaternary ammonium salt indicated by the following chemical formula 4 is preferably used. Here, in chemical formula 4, $R^{10}$ represents an alkyl group having 6 to 18 carbon atoms or $(C_6H_5)$—$CH_2$—, each of $R^{11}$, $R^{12}$ and $R^{13}$ represents an alkyl group or a benzyl group having 1 to 3 carbon atoms, and $Y^-$ represents a halogen ion. Here, $R^{11}$, $R^{12}$ and $R^{13}$ may be the same or different from one another.

Chemical Formula 4

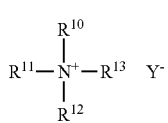

For example, decyltrimethyl ammonium salt, dodecyltrimethyl ammonium salt, tetradecyltrimethyl ammonium salt, hexadecyltrimethyl ammonium salt and octadecyltrimethyl ammonium salt may be preferably used. The amount of use thereof is preferably set in a range from 10 to 30000 mg/l, more preferably, from 100 to 3000 mg/l.

With respect to the dye to be used for the fluorescence-staining treatment of bacteria, not particularly limited, any dye may be used as long as it can stain the bacterial within the above-mentioned pH range. With respect to the concentration, although each dye has a different preferable concentration, it can be set, for example, in a range from 0.1 to 100 ppm (final concentration). Here, from the viewpoint of bacteria detecting capability, the dye to be used is preferably prepared as a fluorescent dye that is combined with at least one of components forming bacteria and emits fluorescence.

More specifically, the dye indicated by the following chemical formula 5 is preferably used. In chemical formula 5, $R_1$ represents a hydrogen atom or an alkyl group having 1 to 3 carbon atoms, each of $R_2$ and $R_3$ represents a hydrogen atom, an alkyl group having 1 to 3 carbon atoms or an alkoxy group having 1 to 3 carbon atoms, $R_4$ represents a hydrogen atom, an acyl group or an alkyl group having 1 to 3 carbon atoms, $R_5$ represents a hydrogen atom or an alkyl group having 1 to 3 carbon atoms that can be substituted, Z represents a sulfur atom, an oxygen atom or a carbon atom substituted with an alkyl group having 1 to 3 carbon atoms, n indicates an integer of 1 or 2, and X— represents anion.

Chemical Formula 5

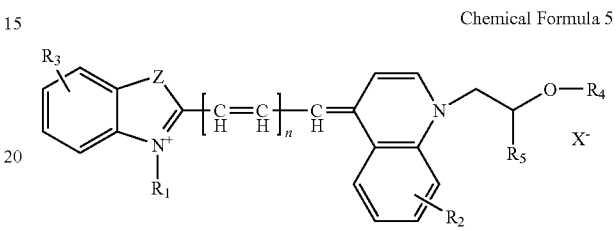

Here, the diluting fluid (first diluting fluid), which is used for measuring the four kinds of particles other than the bacteria, that is, white blood cells, red blood cells, epithelial cells and columnar cells, in a urine sample, is preferably adjusted in such an osmotic pressure range and a pH range as not to hemolyze red blood cells.

In order to adjust the first diluting fluid in such an osmotic pressure range and a pH range as not to subject red blood cells to hemolyzation, it is preferable to add a buffer agent and an osmotic-pressure compensating agent to the first diluting fluid. The pH of the first diluting fluid is preferably set in a range from 3.8 to 10.5, more preferably, from 6.3 to 8.5. This range is set because, when the pH of the first diluting fluid shows a highly alkaline property, red blood cells tend to be hemolyzed, and because in acidic range, the pH change in a urine specimen becomes greater to cause damages to red blood cells and deterioration in the staining property of particles in urine as a whole.

With respect to the buffer agent to be added to the first diluting fluid, those conventionally known agents can be used. For example, Good's buffer agents and the like, such as Tris, MES, Bis-Tris, ADA, PIPES, ACES, MOPSO, BES, MOPS, TES, HEPES, DIPSO, TAPSO, POPSO, HEPPSO, EPPS, Tricine, Bicine and TAPS, may be used. The concentration of the buffer agent to be used is normally set in a range from 20 to 500 mM, more preferably, from 50 to 200 mM.

With respect to the osmotic-pressure compensating agent to be added to the second diluting fluid, inorganic salts, organic salts such as propionic acid salt, and sugars may be used. With respect to the inorganic salts, sodium chloride, potassium chloride, sodium bromide and the like are used. With respect to the propionic acid salt of inorganic salts, sodium propionate, potassium propionate, ammonium propionate and the like are used. With respect to the other organic salts, oxalic acid salts, acetic acid salts and the like are used. With respect to sugars, sorbitol, glucose, mannitol and the like are used. The osmotic-pressure compensating agent is added so as to prevent hemolyzation of red blood cells and obtain a stable intensity of fluorescence. The osmotic pressure of urine is distributed over a wide range of 50 to 1300 mOsm/kg. When the osmotic pressure of an analyzing reagent is too low, the hemolyzation of red blood cells progresses earlier, while, when the osmotic pressure thereof is too high, the particles in the urine sample are greatly damaged; therefore, the osmotic pressure is preferably set in a range from 100 to 600 mOsm/kg, more preferably, from 150 to 500 mOsm/kg.

Moreover, in order to reduce adverse effects from non-crystalline salts appearing in a urine sample (for example, ammonium phosphate, magnesium phosphate, calcium carbonate), a chelate agent used for dissolving these may be added to the diluting fluid for the four particles. With respect to the chelate agent, not particularly limited in the kinds, any chelate agent may be used as long as it serves as a decalcium agent or a demagnesium agent. Examples thereof include: EDTA salt, CyDTA, DHEG, DPTA-OH, EDDA, EDDP, GEDTA, HDTA, HIDA, Methyl-EDTA, NTA, NTP, NTPO and EDDPO. More preferably, EDTA salt, CyDTA and GEDTA are used. The concentration thereof is set in a range from 0.05 to 5 w/w %, more preferably, from 0.1 to 1 w/w %. Here, the decalcium agent or the demagnesium agent refers to an agent that is combined with a calcium ion or a magnesium ion to form a water soluble compound.

When yeast-like fungi appear in a urine sample, the intensity of front scattered light and fluorescence detected from the yeast-like fungi is overlapped with the intensity of those detected from red blood cells to make it difficult to distinguish these. Therefore, a substance that causes a difference between the yeast-like fungi and red blood cells in the staining property to the fluorescent dye may be added to the diluting fluid for particle components. By adding such a substance, the difference is generated between the intensities of fluorescence derived from the yeast-like fungi and the red blood cells so that the distinguishing precision of red blood cells can be improved. With respect to the substance, those substances that give damages to the cell membrane of yeast-like fungi to accelerate the dye permeability to the inside of the cells, with no damages being given to the cell membrane of red blood cells are used. When the cell membrane of red blood cells is damaged, hemolyzation is caused, making it difficult to count the number of the red blood cells. With respect to the substances that satisfy the above-mentioned conditions, non-ionic organic compounds having a benzene ring are preferably used. Examples thereof include: aromatic alcohols, such as benzyl alcohol, β-phenethyl alcohol, phenol, 1-phenoxy-2-propanol and 2-phenoxy ethanol, thiazole-based compounds such as 2-aminobenzothiazole and benzothiazole, and phenyl acetate.

Here, in the present embodiment, with respect to the particles that can be stained and the fluorescent dye used for staining particle components in a urine sample, condensed benzene derivatives represented by the following Chemical Formula 6 and Chemical Formula 7 can be used.

Chemical Formula 6

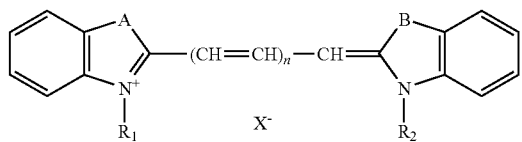

In Chemical formula 6, each of $R_1$ and $R_2$ represents a hydrogen atom, or an alkyl group having 1 to 6 carbon atoms, or an alkyl group having 1 to 6 carbon atoms, which is substituted by a hydroxide group. A and B represent sulfur, oxygen, nitrogen, or carbon having a lower alkyl group selected from methyl and ethyl. Moreover, n is an integer of 1 or 2, and $X^-$ is an anion.

Chemical Formula 7

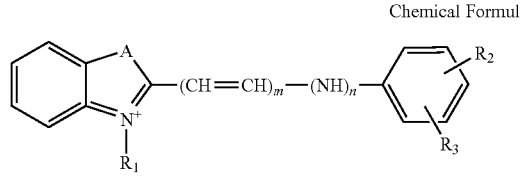

In Chemical formula 7, $R_1$ represents an alkyl group having 1 to 6 carbon atoms. $R_2$ represents a hydrogen atom, or an alkoxy group having 1 to 3 carbon atoms. $R_3$ represents an alkoxy group having 1 to 3 carbon atoms, or a lower dialkyl amino group substituted by an alkyl group having 1 to 3 carbon atoms, or $N(CH_3)C_2H_4CN$. A represents sulfur, oxygen, or carbon having a lower alkyl group selected from methyl and ethyl. Moreover, m is 1 or 2, and n is 0 or 1.

The above description has discussed the embodiment in which the standard material of the present invention is applied to the analyzer 1 for analyzing particle components in urea which prepares the measuring sample A used for measuring the four kinds of particles, that is, white blood cells, red blood cells, epithelial cells and columnar cells and the measuring sample B used for measuring bacteria by using a sample preparing part and carries out measuring processes; however, the present invention is not intended to be limited by the above-mentioned embodiment. The standard material of the present invention can be applied to any analyzer as long as it is a particle analyzer provided with a sample preparing part that carries out a fluorescence-staining treatment on particles in a biological sample and a fluorescence detector. For example, the particle analyzer of this type is prepared as an analyzer in which, in the analyzer 1 for analyzing particle components in urea, sample preparing parts used for measuring bacteria (containers 20 and 21, syringe pumps 22 and 23, and a reaction chamber 18) are not installed, with a single sample preparing part (containers 24 and 25, syringe pumps 26 and 27, and a reaction chamber 19) being used for preparing a measuring sample used for measuring white blood cells, red blood cells, epithelial cells and columnar cells.

The standard material relating to the present invention is effectively applied as a standard material to be used for quality-controlling processes or calibration processes in an automatic particle analyzer.

What is claimed is:

1. A method for judging an abnormal portion in a particle analyzer which comprises a measuring sample preparation unit for preparing a measuring sample by mixing a biological sample with a first fluorescence dye, a light source for irradiating the measuring sample with light and a fluorescence detector for detecting fluorescence from the measuring sample, comprising steps of:
    detecting first fluorescence from first standard particles and second fluorescence from second standard particles by using the particle analyzer; and
    first comparing the first fluorescence with a first condition corresponding to expected fluorescence of said first standard particles defined by predetermined upper and lower limit values; and
    second comparing the second fluorescence with a second condition corresponding to expected fluorescence of said second standard particles defined by predetermined upper and lower limit values; and judging the abnormal portion in the particle analyzer based upon the first fluorescence and the second fluorescence;

wherein the first standard particles can be fluorescence-stained by the fluorescence staining treatment, and wherein the second standard particles have preliminarily contained a fluorescence dye; and wherein the judging step judges the abnormality in the fluorescence detector based upon the second comparison result and judges the abnormality in the sample preparation unit based upon the first comparison result and the second comparison result; and wherein the abnormalities correspond to values outside said predetermined upper and lower limit values.

2. The method according to claim 1, further comprising a step of preparing the measuring sample by mixing the first fluorescence dye with a standard material containing the first standard particles and the second standard particles, and the first fluorescence and the second fluorescence being detected from the first standard particles and the second standard particles contained the measuring sample.

3. The method according to claim 1, further comprising steps of:

first preparing the first measuring sample by mixing the first fluorescence dye with a first standard material containing the first standard particles; and second preparing the second measuring sample by mixing the first fluorescence dye with a second standard material containing the second standard particles;

wherein the detecting step detects the first fluorescence from the first standard particles contained in the first measuring sample and detects the second fluorescence from the second standard particles contained the second measuring sample.

4. The method according to claim 1, wherein the particle analyzer comprises a scattered light detector for detecting scattered light from the measuring sample, the detecting step further detects first scattered light from the first standard particles and second scattered light from the second standard particles, and the judging step judges the abnormality in the scattered light detector based upon the first scattered light and the second scattered light.

5. The method according to claim 1, wherein the second standard particles actually are not stained by the first fluorescence dye.

* * * * *